United States Patent
Sirovich (10) Patent No.: US 9,672,271 B2
(45) Date of Patent: Jun. 6, 2017

(54) METHOD FOR IDENTIFYING AND EMPLOYING HIGH RISK GENOMIC MARKERS FOR THE PREDICTION OF SPECIFIC DISEASES

(71) Applicant: Lawrence Sirovich, New York, NY (US)

(72) Inventor: Lawrence Sirovich, New York, NY (US)

( * ) Notice: Subject to any disclaimer, the term of this patent is extended or adjusted under 35 U.S.C. 154(b) by 38 days.

(21) Appl. No.: 14/268,982

(22) Filed: May 2, 2014

(65) Prior Publication Data

US 2014/0344272 A1 Nov. 20, 2014

Related U.S. Application Data

(60) Provisional application No. 61/824,703, filed on May 17, 2013.

(51) Int. Cl.
  *G01N 33/50* (2006.01)
  *G06F 17/30* (2006.01)
  *G06F 19/18* (2011.01)
  *G06F 19/24* (2011.01)

(52) U.S. Cl.
  CPC ........ *G06F 17/30598* (2013.01); *G06F 19/18* (2013.01); *G06F 19/24* (2013.01)

(58) Field of Classification Search
  None
  See application file for complete search history.

(56) References Cited

U.S. PATENT DOCUMENTS

| | | |
|---|---|---|
| 7,272,506 B2 | 9/2007 | Glanowski et al. |
| 2004/0132015 A1 | 7/2004 | Lee et al. |
| 2010/0285980 A1 | 11/2010 | Shak et al. |
| 2011/0014607 A1 | 1/2011 | Jirtle et al. |
| 2011/0238318 A1 | 9/2011 | Cooney |

*Primary Examiner* — Jason Sims
(74) *Attorney, Agent, or Firm* — Lackenbach Siegel LLP; Myron Greenspan (57) ABSTRACT

A reorganization of genomic data into a simpler standard form leads to more transparent data analyses. The customary selection practice that focuses on high odds ratios loci is shown to be biased, reflecting quality of presently reported risk loci for T2D. A selection criterion, based on Shannon information theory, brings clarity to this issue and provides a rational and optimal basis for selecting potential risk loci. This is used to determine an optimal disease classifier. Within the framework of the FUSION database this leads to a relatively successful degree of T2D prediction and nearly an order of magnitude more effective in detecting T2D. Chromosome 7 is strongly associated with T2D. A hypothesis of this study is that the genomic disease signal is possibly weak, and instead of focusing on individual loci a collection of loci contribute to a composite Score, which functions as the determinant of disease or its absence.

14 Claims, 4 Drawing Sheets

|   | Seq. No. | |
|---|---|---|
| 1 rs3934634 | 1 | TCCCTCCCCCGCCCTCCCGCTCCCCCCC |
| 1 rs3737728 | 2 | GGAAGGGAGAGGGGGGGAAGGGGGAG |
| 1 rs6687776 | 3 | TCTCCCCCCCCCCCTGTCTCCCCCCCCC |
| 1 rs9651273 | 4 | GGAGAGGGAGAGGGGGAGAGGGAGGGGG |
| 1 rs4970405 | 5 | AAAAAAAAAAAAAAAAAAAAAAAAAAAA |
| 1 rs12726255 | 6 | AAAAAAAAAAAAAAAAAAAAAAAAAAAA |
| 1 rs2298217 | 7 | CCTCCCCCCCCCGCCCGCTCCCCCCCCC |
| 1 rs4970357 | 8 | AAAAAAAAACCAACAAAAAAAAAAAAA |
| 1 rs4970362 | 9 | GGAGGGAGAAGGAGAGGGGGAGAGAA |
| 1 rs9660710 | 10 | CCCCCCCCCCAACCACCCCCCCCCCCCCC |
| 1 rs4970420 | 11 | AGGGGAGGGGGGGGGGCGAAGAAGG |

Fig. 4

| 1 | Locus | ... | N | N+1 | N+2 | N+3 | N+4 | ... |
|---|---|---|---|---|---|---|---|---|
| 2 | Snps | ... | (A,T) | (C,G) | (C,T) | (A,T) | (A,G) | ... |
| 3 | Acquired Sequence | ... | AT | CC | TT | TA | AG | ... |
| 4 | Standard Form | ... | TA | CC | TT | TA | GA | ... |
| 5 | Alias | ... | 21 | 11 | 22 | 21 | 21 | ... |
| 6 | Binary | ... | 10 | 00 | 11 | 10 | 10 | ... |

| rs 3934834 | rs 3737728 | rs 6687776 | rs 9651273 | rs 4970405 |
|---|---|---|---|---|

Fig. 5

SEQUENCE LISTING

```
<160> NUMBER OF SEQ ID NOS: 12

<210> SEQ ID NO 1
<211> LENGTH: 27
<212> TYPE: DNA
<213> ORGANISM: Homo sapiens

<400> SEQUENCE: 1
tccctccccc ccctccccc tccccc                                27

<210> SEQ ID NO 2
<211> LENGTH: 29
<212> TYPE: DNA
<213> ORGANISM: Homo sapiens

<400> SEQUENCE: 2
ggaaagggag agagggggga aggggggag                             29

<210> SEQ ID NO 3
<211> LENGTH: 28
<212> TYPE: DNA
<213> ORGANISM: Homo sapiens

<400> SEQUENCE: 3 tctcccccc ccctctctc ccccccc                                 28
```

```
<210> SEQ ID NO 4
<211> LENGTH: 28
<212> TYPE: DNA
<213> ORGANISM: Homo sapiens

<400> SEQUENCE: 4
ggagagggag aggggagag ggagggg                                              28

<210> SEQ ID NO 5
<211> LENGTH: 26
<212> TYPE: DNA
<213> ORGANISM: Homo sapiens

<400> SEQUENCE: 5
aaaaaaaaaa aaaaaaaaaa aaaaaa                                              26

<210> SEQ ID NO 6
<211> LENGTH: 28
<212> TYPE: DNA
<213> ORGANISM: Homo sapiens

<400> SEQUENCE: 6
aaaaaaaaaa aaaaaaaaaa aaaaaaaa                                            28

<210> SEQ ID NO 7
<211> LENGTH: 28
<212> TYPE: DNA
<213> ORGANISM: Homo sapiens

<400> SEQUENCE: 7
cctccccccc ccccccctc ccccccc                                              28

<210> SEQ ID NO 8
<211> LENGTH: 28
<212> TYPE: DNA
<213> ORGANISM: Homo sapiens

<400> SEQUENCE: 8
aaaaaaaaaa ccaacaaaaa aaaaaaaa                                            28

<210> SEQ ID NO 9
<211> LENGTH: 28
<212> TYPE: DNA
<213> ORGANISM: Homo sapiens

<400> SEQUENCE: 9
ggagagggag aaggagaggg ggagagaa                                            28

<210> SEQ ID NO 10
<211> LENGTH: 28
<212> TYPE: DNA
<213> ORGANISM: Homo sapiens

<400> SEQUENCE: 10
cccccccccc aaccaccccc ccccccc                                             28

<210> SEQ ID NO 11
<211> LENGTH: 28
<212> TYPE: DNA
<213> ORGANISM: Homo sapiens

<400> SEQUENCE: 11
```

-continued aggggggaggg gggggggggg aaagaagg                    28

<210> SEQ ID NO 12
<211> LENGTH: 10
<212> TYPE: DNA
<213> ORGANISM: Homo sapiens

<400> SEQUENCE: 12
tacctttaga                                         10

METHOD FOR IDENTIFYING AND EMPLOYING HIGH RISK GENOMIC MARKERS FOR THE PREDICTION OF SPECIFIC DISEASES

The contents of the Electronic Sequence Listings filed herewith (Sequences_ST25.txt: Size 2062 bytes; and Date of Creation: Jul. 7, 2014) is herein incorporated by reference in its entirety.

BACKGROUND OF THE INVENTION

1. Field of the Invention

The present invention relates in general terms to DNA genotypic data that is linked to clinical diagnosis, phenotypic data. More particularly a method is presented for extracting genomic classifiers of disease risk from genomic data as obtained from micro array or gene chip assays in conjunction with their phenotypic correlates. This leads to methods of disease forecasting and individual patient disease risk prediction; as well as to devices which accomplish these goals.

2. Description of the Prior Art

There are almost three billion (coding and non-coding) DNA base pair in the human genome, with about 99.5% of these are shared by all *homo sapiens*. Each somatic cell contains a maternal and a paternal contribution; so the overwhelming contribution is homozygous, but the remaining pairs appear as two alleles. These noteworthy deviant markers are termed the S(ingle) N(ucleotide) P(olymorphism)—SNPs, which are heterozygous pairs or alleles. By definition for the allele pair to be a SNP the rarer allele frequency must be greater than 1% in the population. A SNP for which both alleles produce the same polypeptide sequence is said to be a silent (synonymous) mutation. If a different polypeptide occurs it is said to be a replacement polymorphism. There is a general view that this subset of the genome accounts for human variations, and in particular carries the potential for acquiring diseases. Replacement polymorphisms, which result in polypeptide substitution, are thought to be responsible for over half the known diseases of mutagenic origin (Stenson et al., 2009).

DNA genotyping is performed by microarrays, also referred to as a gene chips. This is a collection of microscopic DNA spots attached to a solid surface; referred to as reporters or probes. A single chip can contain many hundreds of thousands of probes. While polymerase chain reaction (PCR) microarrays, or gene chips, have facilitated acquisition of vast quantities of genomic data, disappointment has been expressed on the lack of DNA variant linkages to human diseases particularly in the case of complex disorders (Chakravarti, 2011).

Patents exist that associate SNPs with genetic-based diseases. For example, in U.S. Patent Publication No. US2004/0132015 a process is disclosed for detecting mutations in regions determined by codon scanning algorithm. A process for preparing the DNA chip is disclosed using the process, as is the method for detecting mutations using DNA chips. Mutations can be discerned as various genetic diseases and this can be detected and identified, the DNA chip using the codon scanning algorithm can be applied for diagnoses of genetic mutations-associated diseases.

A computer algorithm for mathematical allele combination from a gene type device is disclosed in U.S. Pat. No. 7,272,506. The patent discloses an automated method for identifying allele values from a data file and analyzing polymorphisms DNA. The method is used for distinguishing targeted polymorphisms DNA sites without control samples.

U.S. Patent Publication No. US 2011/0014607 discloses methods for identifying imprinted genes. In some of the methods a first data set is provided of a plurality of nucleic acid sequences corresponding to a plurality of genes known to be imprinted in a subject. A second data set includes a plurality of nucleic acid sequences corresponding to genes known not to be imprinted into a subject. One or more features are identified that, by themselves or combinations, are differentially present or absent from the first data set as contained with the second data set. One or more features are applied to a test data set comprising a plurality of genomic DNA sequences that correspond to one or more genes for which an imprinting status is unknown to identify and imprint gene in a subject. The '607 Publication also discloses a method for identifying a feature in the subject with respect to an imprinted gene and methods for detecting the presence of susceptibility to a medical condition associated with parent-of-origin dependent monoallelic expression in the subject.

An algorithm for quantifying polymorphisms in an electropherogram as disclosed in U.S. Patent Publication No. US 2011/0238318. This Publication discloses a method of quantifying particular target cite of a cell or organism by performing genomic sequencing in which the DNA sample is extracted from a cell or organism and after being treated to convert cytosine to uracil and a fragment of the treated DNA is amplified. A sequence analysis is then performed from an electropherogram from which calculations can be made to perform a sequence analysis.

U.S. Patent Publication No. US 2010/0285980 discloses a gene expression profile algorithm that provides a test for likelihood of recurrence of colorectal cancer and response to chemotherapy that involves analysis of gene expression values of prognostic and/or predictive genes. A biological sample can be obtained from a cancer patient. The measure of the expression levels to provide such information is analyzed and other methods of analysis are disclosed to identify genes that co-express with a validated biomarker that may be substituted by that biomarker in an assay is also disclosed.

SUMMARY OF THE INVENTION

The invention uses microarray genotyping data and reformulates the data in a new and unique allelic form which facilitates genetic marker classification of disease risk by novel and expeditious means; this may be an enabler of "personalized medicine"—a proposed avenue for dealing with disease association. As recently as Oct. 7, 2011 a *Science* editorial refers to present methodologies as a gaping hole. The present discoveries provide new approaches for the successful isolation of a kernel of genomic markers associated with a disease, and for the first time offers a successful way for proper analyses and prediction of multi-marker complex diseases.

The features of this invention are contained in the following elements:

1. Development of a novel reorganization of genomic DNA sequences which standardizes the order and acquisition of individual alleles.

2. Emphasis on an unambiguous allele locus, instead of the universally used SNP pair, that now results in a significantly enhanced discovery procedure for risk loci related to disease.

3. A new theoretical analysis, based on the premise that disease represents a small signal immersed in large genomic databases and which then produces a disease classifier and a composite Score yielding disease prognosis.

4. A new method for marker discovery that produces unbiased selection of high value potential disease risk loci.

5. A method for incorporating the contributions of a large number of genomic loci for grading the risk of disease; this may be cause of the present failure to predict, since most studies focus on single SNPs.

Consequences of those elements are the following:

An algorithm for detecting genomic markers associated with disease by contrasting these with non-disease controls.

A method for ordering markers in terms of their value for disease association.

A method for eliminating environmental, cultural, ethnic and other irrelevant elements from disease consideration.

An algorithm for isolating the classifier set, a particular case being the indicator vector for type 2 diabetes, T2D.

BRIEF DESCRIPTION OF DRAWINGS AND METHODS

Those skilled in the art will appreciate the improvements and advantages that derive from the present invention upon reading the following detailed description, claims, and drawings. Further details are in Sirovich 2014a, 2014b both attached.

DESCRIPTION OF PREFERRED EMBODIMENTS

Figure 1:
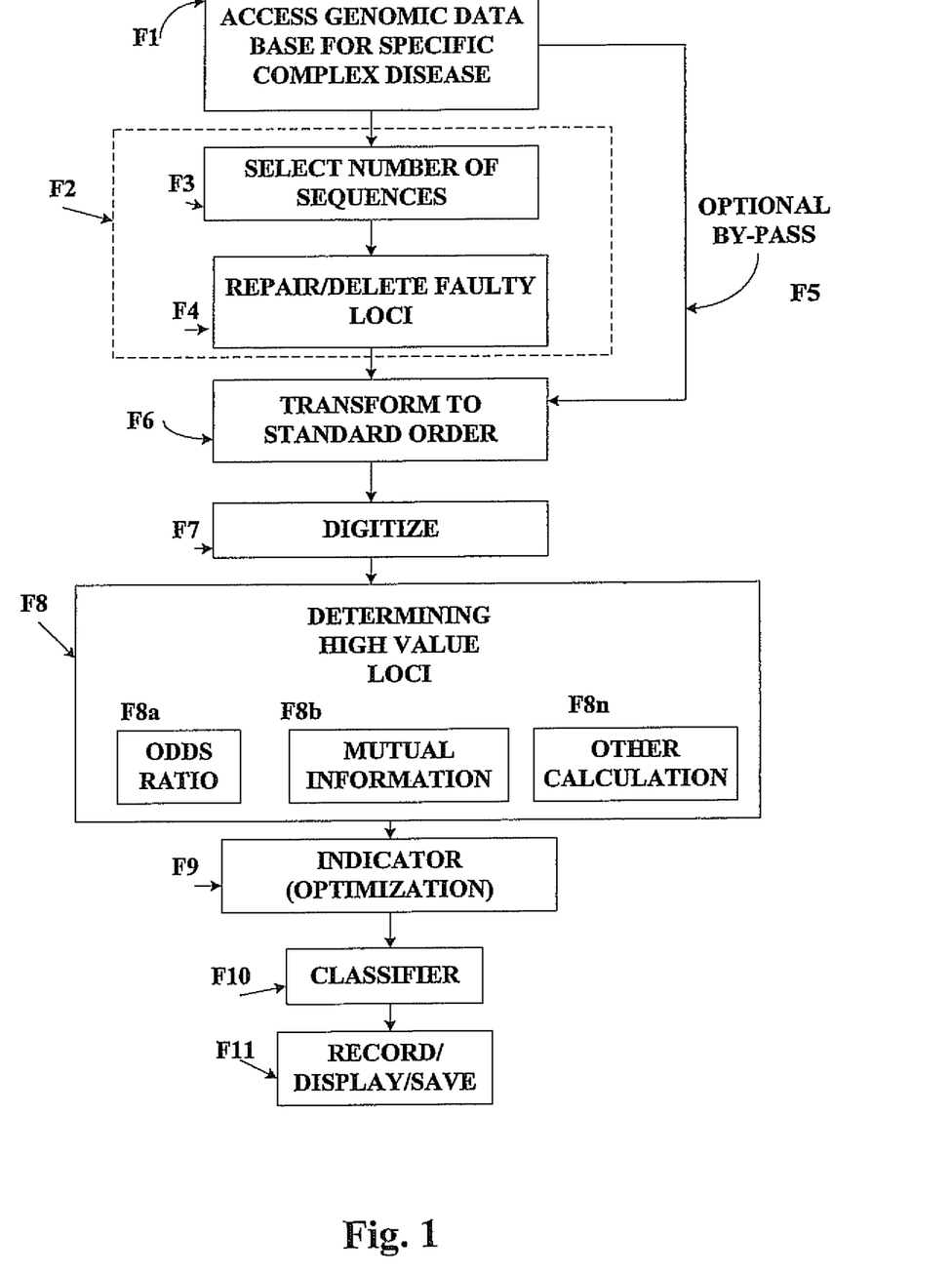
FIG. 1 is a flow diagram illustrating the components and method steps or processes for implementing the invention and to generate and test a classifier of disease. This will be illustrated for the case of type 2 diabetes based on the Finland-United States Investigation of NIDDM Genetics (FUSION) study database.

FIG. 1 depicts the flow diagram of the invention which illustrates the general treatment of a disease/control database. This is illustrated below with the FUSION database.

Technical Details

An outline of the algorithmic processes is furnished in the flow diagram which describes the components and the steps in the overall algorithmic procedures. Further details of the methods and their algorithmic connections are presented below in relation to FIG. 1.

1. Step F1—Accessing FUSION Database

In Step F1 of FIG. 1 a genomic database for a complex disease is accessed, which is illustrated by type 2 diabetes (T2D), obtained from the National Institutes of Health.

Figure 4:
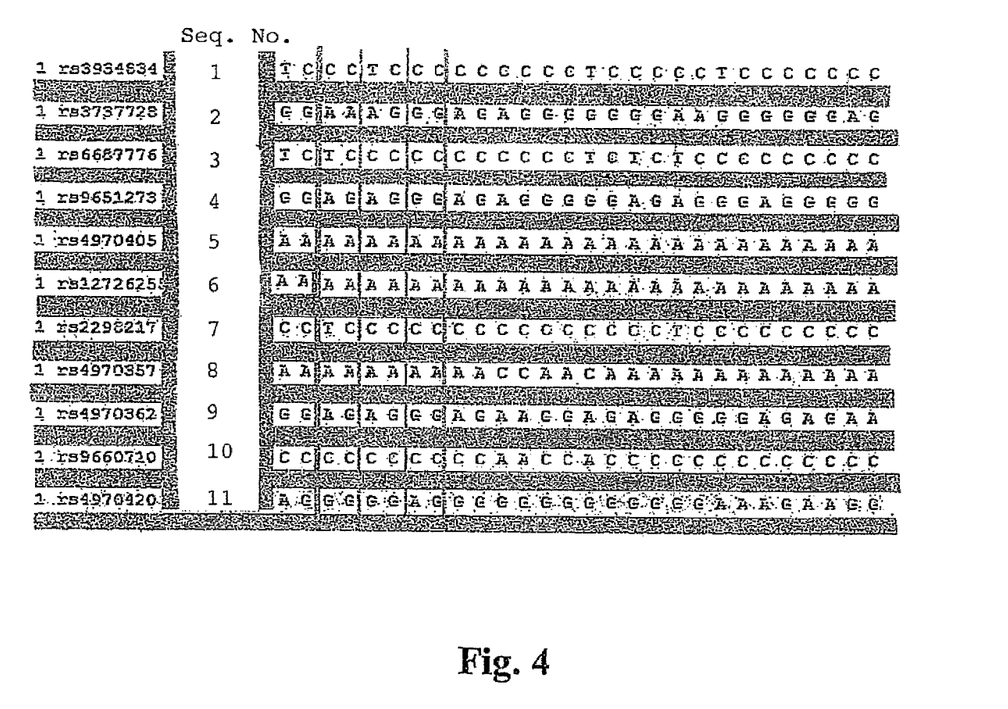
FIG. 4 is a sample of genomic data in the database used in the disclosed example of the invention.

The methods of this application are based on clinically linked genomic data. The framework of the methods will be illustrated for type 2 diabetes, T2D: Finland-United States Investigation of NIDDM Genetics (FUSION) study, NIH-dbGap. Details of the database are as follows:

919 T2D cases, 787 normal glucose tolerant (NGT) controls; 315693 Common SNPs, FIG. 4 shows a sample of the database. Rows show SNP pairs (Sequences 1-11), identified by rs numbers which locate chromosome, position on the chromosome and the allele pair of symbols.

2. Step F2—Data Preparation

The data contained in the database (F1) may contain irrelevant sequences or faulti loci. The data set so accessed may be optionally prepared to facilitate or expedite analysis or enhance the accuracy of the results. Such preparation may include selection of the number of sequences (at F3) and/or repair or delete faulty loci (at F4) as shown in FIG. 1.

Repair/Delete Faulty Loci—F4

Normally acquired data by gene chips contains a relatively low level of missing data. Data management tools such as Matlab, the 'R' programming language, or the 'Plink' toolset, (the last two are publicly available), easily accomplish this task. In accordance with the example being described the method focuses primarily on loci with fewer than 2 missing symbols, reducing the number of SNPs to 272,423; and replacing remaining missing symbols by appropriate column mode symbols.

Selection of a limited number of sequences (Step F3) is optional and no such restriction is required although it has been determined that comparable results will be obtained. Also, repairing and/or deleting faulty loci (Step F4) is optional. However, data preparation (Steps F3 and/or F4) does improve the results.

If the data is not to be "prepared" at F2 step 2 may be by-passed, at F5, in which case all the native data accessed at F1 is used, as to be described.

3. Step F6—Transform Data to Standard Order

Figure 5:
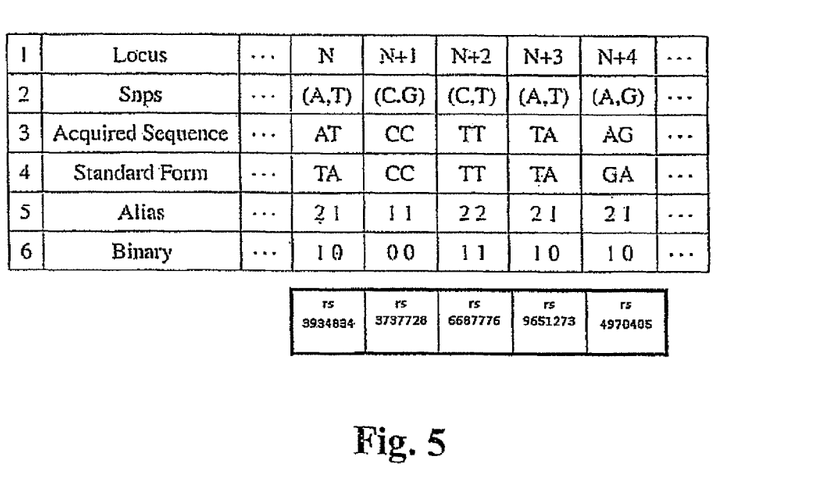
FIG. 5 shows a string of five SNPs with the known symbols given on line 2, how they might be acquired on line 3, the standard form on line 4, aliased on line 5, and line 6 an alternate abasing in binary form.

The nth SNP of a database sequence is registered as two alleles indexed as, (2n−1,2n) and referred to as the odd and even members of the SNP pair. According to the standard order introduced here the higher symbol will be move to the odd position and aliased as a 2 and the lower symbol moved to the even position and aliased by 1. No information is lost since the accompanying rs number (part of database) of a SNP fully furnishes location and alleles. The information at a SNP of a sequence is determined by whether 22, 21 or 11 is registered. The steps that are followed are outlined in FIG. 5. This we refer to as the standard order, a novel reorganization of genomic sequences with highly important consequences. The required transformations can be easily accomplished by the above mentioned software.

4. Step F7—Digitalization of Symbols F5

Transformation of the alias symbols "1" & "2" into a digital form is achieved by the vectorization $$1 \to [1,0], 2 \to [0,1]. \tag{1}$$

For a typical sequence S this gives the symbol to vector formulation $$S=(T,A,C,C,T,T,T,A,G,A) \to [0,1,1,0,1,0,1,0,0,1,0,1,0,1, 0,0,1,1,0]. \tag{2) (Sequence No. 12)}$$

Other equivalent aliasing symbols can be used.

The required transformations can be easily accomplished by the above mentioned software.

5. Step F8—Determining High Value Markers or Loci

A feature of the invention is the examination of the digitized data to determine the high value markers or loci. The examination, at F8, involves identifying those markers or loci that reflect, relate to or are associated with the specific disease using a suitable mathematical model, typically a statistical model, that compares the data base for both disease and control loci. Best results have been found when the statistical model eliminates or minimizes biased sampling. Examples of such mathematical models includes the use of Odds Ratios (RO), at F8a, and/or Incremental Information (M), at F8b. However, other models, at F8$_n$, are possible and sampling models developed in the future are contemplated if these reduce bias and provide more accurate, consistent or reliable results.

For a collection of M sequences, at any SNP the probability at an odd allele, p$^o$ (2), is easily calculated as the frequency of symbol 2 at the odd position and similarly p$^e$(1) is the probability of symbol 1 the even allele.

The probability of a 22 SNP pair, P(22), is then given by $$P(22)=1-p^e(1), \quad (3)$$

similarly the probability of a 11 SNP pair is $$P(11)=1-p^o(2), \quad (4)$$

and from this the SNP probability of a 21 pair is $$P(21)=1-P(22)-P(11). \quad (5)$$

If P1) denotes the probability of symbol 2 for a SNP then $$P(1)=1-P(2). \quad (6)$$

This reduces all allele and SNP probabilities to simple steps.

It should be noted that the symbols 2 & 1 are the designated symbols at the odd and even alleles, but they might not be the most probable symbols at a locus, for example the data might dictate that at some locus p$^o$(1)>p$^o$(2), in which case the non designated symbol is the most probable. To make this clear this can be written as follows:

$$\text{probability of most probable allele: } \Pi \quad (7)$$

$$\text{probability of rarer allele: } \Theta=1-\Pi \quad (8)$$

Odds Ratios (F8a)

The allele odds-ratio is given by $$\omega(p) = \frac{p_d/(1-p_d)}{p_c/(1-p_c)} = \frac{p_d q_c}{p_c q_d} = 1/\omega(q), \quad (9)$$

Where the subscripts d & c refer to the disease and control cases, and odds ratios are a standard way for contrasting the two conditions. This for example is a standard package contained in the Plink toolbox. The SNP counterpart will be denoted by $\Omega$, which as shown in Sirovich, 2014a, 2014b and here later is less effective than (9). Large values of the odds-ratios have been generally regarded as potentially being associated with disease risk.

It is a general observation that for genomic data that p$_d$ and p$_c$ are not very different, and to explore this consider $$p_d = p_c + \Delta \quad (10)$$

with $\Delta$ relatively small. Hence the odds-ratio $\omega$, (9), becomes $$\omega = 1 + \frac{\Delta}{p_c(1-p_c)-p_c\Delta} \approx 1 + \frac{\Delta}{p_c(1-p_c)}, \quad (11)$$

so that $\omega$ is large if p$_c \approx$ 0 or 1, thus indicating a possible strong unwanted selection bias.

Incremental Information (F8b)

Shannon (1948) has demonstrated that entropy, $$S(p)=-(p \ln p+(1-p)\ln_2(1-p))=-\ln_2 p^p q^q = S(q) \quad (12)$$

provides an optimal basis for unbiased sampling, Jaynes (1955). (Here we again follow common convention that if p is the probability of one of two events then $$q=1-p, \quad (13)$$

is the probability of the second event.) In the present situation (12) leads to incremental information sampling $$M=S_d-S_c, \quad (14)$$

which the counterpart to the odds ratio. Under the approximation (10) this yields $$M = \Delta\left(\frac{1-p_c}{p_c}\right) \quad (15)$$

Figure 3:
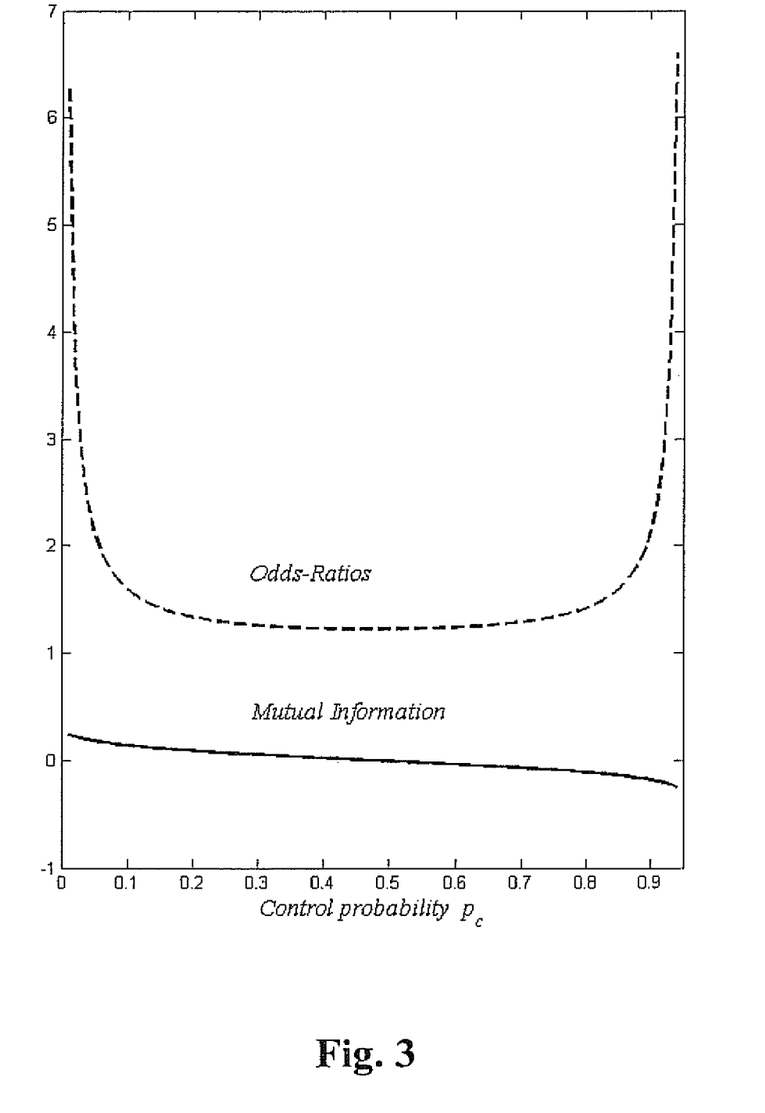
FIG. 3 compares odds-ratio versus incremental information selection of high value markers.

FIG. 3 compares (11) and (15) for the nominal value of $\Delta$=0.05. This clearly illustrates the assertion that the odds-ratios leads to biased sampling while incremental information does not do so. Note that (12) and hence (14) vanishes at p=0 or 1, and that the neighborhood of these points is avoided in using incremental information. Thus to reduce computation alleles at which the probability p>0.99 or <0.01. are removed from consideration.

6. Step F9—Indicator Vector with v suitably normalized, and the columns of C and D are restricted to the chosen set of high risk loci, which might emerge from odds ratios, incremental information or from some other method of choosing the admissible range of risk alleles.

The process of optimizing the above criterion falls under the category of standard mathematics and an explicit indicator v that emerges explicitly from typical eigenvector software that can be found universally and in particular in Matlab and R. There are two parts to the solution, one is a reduced set of allele locations, and the second part are the indicated risk symbols at the corresponding loci; which is the classifier and in a general sense is a word. The indicator is a two row matrix, the first giving the loci and the second the classifier 'word'. A sequence viewed in the space of loci defined by the first row of the indicator vector will be scored by the sum of loci at which recorded symbols agree with the Classifier F10 of FIG. 1. Thus in FIG. 2 the maximum agreement score is 1,355.

4. Step F10—T2D Classifier

Scoring

Figure 2:
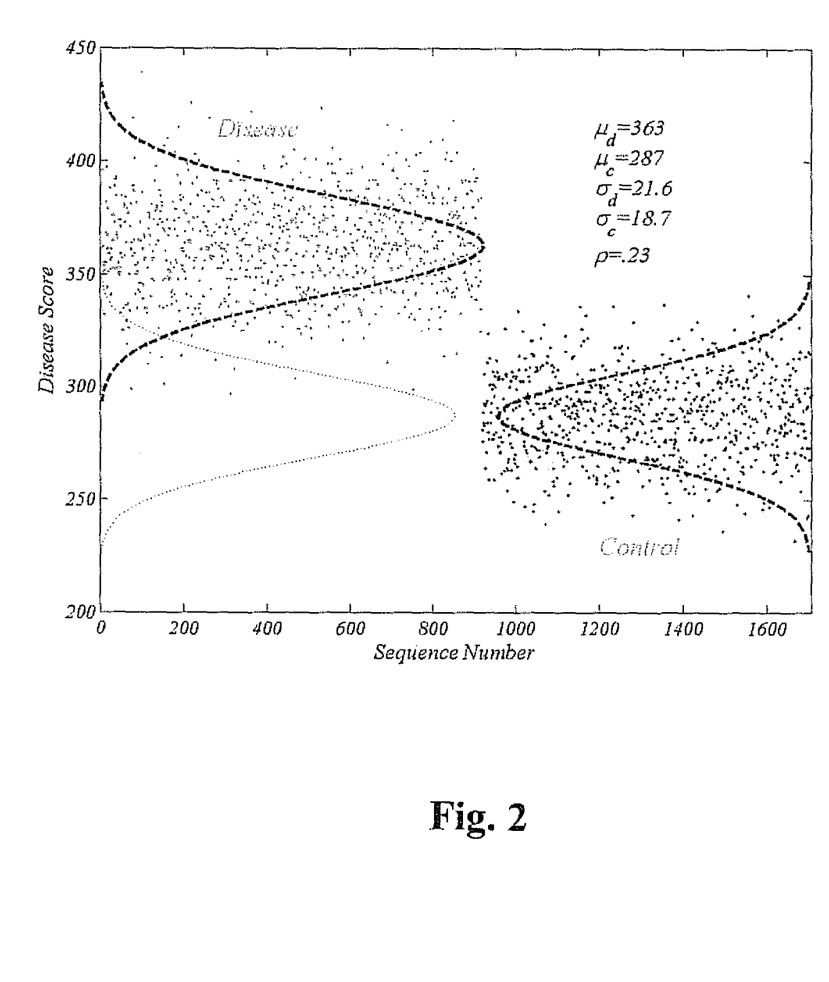
FIG. 2 illustrates agreement scores of the incremental information T2D classifier for the populations, the error is roughly a ½ percent.

Scoring for the FUSION database is displayed in FIG. 2 for the case and control populations and its role is indicated in the FIG. 1 flow diagram. The number of false positives plus false negatives was 10 out of 1706 sequences in what is a self consistency validation.

Additional details and further background is contained in the attached Sirovich 2014a & 2014b publications.

Incremental Information Results

For type 2 diabetes, (T2D), database the nominal incremental information criterion $$M>0.07, \quad (18)$$

produces roughly 15,000 potential high risk loci, which as mentioned above will be referred to as the admissibility class. This is a relatively large number which includes such unwanted contributions as environmental factors, cultural and ethnic elements and other unknown irrelevant effects in addition to the actual loci of the specific disease in question. It is the role of the indicator analysis to optimally eliminate the unwanted elements while retaining the disease related loci. The classifier for T2D as determined from incremental information indicator analyses contains 1,355 risk loci. (This should to be compared with 4,315 loci when using odds-ratio sampling, Sirovich, 2014a. and therefore represents an immense improvement in precision.) Of more importance is that the resolution factor, p is now roughly 100 times better than was obtained using odds ratio sampling of Sirovich, 2014a. In Table 1 below the top 15 markers out the 1,355 markers for T2D, and their statistics are shown.

The highest value of incremental information is roughly 0.2, and a choice of threshold much greater than 0.07 reduces the size of the admissibility set, e.g. for M>0.09 the size of the admissibility set is ~5300 and the classifier is about 400 in length. Use of this produces a large number of false positives and false negatives. In the same vein a small threshold produces a large admissibility set which overfits the data with a loss of precision. The value in (18) was deemed to be the most suitable over a wide range trials.

mentioned above. The pervasive reason for failure to belong to this admissibility class was the condition that $$Q_d \approx Q_c, \quad (19)$$

which since both rare probabilities are small implies that the odds ratio is large but the incremental information is near zero. It is highly unlikely that a locus of this sort can be a true predictor. Virtually all loci determined on the basis of odds ratios reported in Sirovich, 2014a were wiped out by this condition.

An Example

Allele 347351 is the odd locus of rs2237892, and is a SNP that has been associated in the literature with T2D. For this locus $Q_d$=0.108 and $Q_c$=0.084, and therefore the odds ratio lies in the steep climb at the left of FIG. 3; the SNP odds ratio $\Omega$=1.32. Based on roughly 1000 sequences the control distribution has a standard deviation $\sigma$=0.009 and $Q_d$ is

TABLE 1

| | Identifier | Chromo no. | Mutual info | $P_d$ | $P_c$ | $Q_d$ | $Q_c$ | $Q_d/Q_c$ | Allele OR, $\omega$ | SNP OR, $\Omega$ |
|---|---|---|---|---|---|---|---|---|---|---|
| 1 | rs4598195 | 7 | 0.1916 | 0.8139 | 0.8895 | 0.1861 | 0.1105 | 1.6832 | 1.8394 | 1.1549 |
| 2 | rs854065 | 7 | 0.1805 | 0.8792 | 0.9339 | 0.1208 | 0.0661 | 1.8280 | 1.9418 | 1.1045 |
| 3 | rs6005150 | 22 | 0.1743 | 0.8477 | 0.9085 | 0.1523 | 0.0915 | 1.6652 | 1.7847 | 1.2431 |
| 4 | rs6832679 | 4 | 0.1740 | 0.8596 | 0.9174 | 0.1404 | 0.0826 | 1.6996 | 1.8138 | 1.7290 |
| 5 | rs311346 | 6 | 0.1735 | 0.8716 | 0.9263 | 0.1284 | 0.0737 | 1.7423 | 1.8516 | 1.1868 |
| 6 | rs2237686 | 7 | 0.1733 | 0.8172 | 0.8856 | 0.1828 | 0.1144 | 1.5985 | 1.7324 | 1.1322 |
| 7 | rs11935974 | 4 | 0.1714 | 0.8128 | 0.8818 | 0.1872 | 0.1182 | 1.5838 | 1.7182 | 1.6958 |
| 8 | rs6068047 | 20 | 0.1641 | 0.8683 | 0.9212 | 0.1317 | 0.0788 | 1.6713 | 1.7731 | 1.1282 |
| 9 | rs652054 | 11 | 0.1641 | 0.8248 | 0.8882 | 0.1752 | 0.1118 | 1.5668 | 1.6871 | 1.2301 |
| 10 | rs4840986 | 8 | 0.1622 | 0.8575 | 0.9123 | 0.1425 | 0.0877 | 1.6259 | 1.7299 | 1.2424 |
| 11 | rs7071027 | 10 | 0.1622 | 0.8575 | 0.9123 | 0.1425 | 0.0877 | 1.6259 | 1.7299 | 1.2922 |
| 12 | rs7953729 | 12 | 0.1620 | 0.7878 | 0.8602 | 0.2122 | 0.1398 | 1.5181 | 1.6576 | 1.1864 |
| 13 | rs13232099 | 7 | 0.1616 | 0.8259 | 0.8882 | 0.1741 | 0.1118 | 1.5570 | 1.6745 | 1.5457 |
| 14 | rs1166906 | 1 | 0.1612 | 0.8379 | 0.8971 | 0.1621 | 0.1029 | 1.5753 | 1.6866 | 1.2370 |
| 15 | rs2149739 | 10 | 0.1609 | 0.8596 | 0.9136 | 0.1404 | 0.0864 | 1.6246 | 1.7266 | 1.2896 |

In Table 1 the top 15 loci based on incremental information are listed in column 4. The true allele probabilities of (7) & (8) have been used and the notation of the table follows that convention. Note that the probability of the rarer symbol determines the risk.

The largely improbable multiple and prominent appearance of chromosome 7 in column 3 implies a link of T2D with chromosome 7.

Comparison with Previous Studies

A search of prior T2D studies (Perry et al., 2009; Morris et al., 2012; McCarthy & Zeggini, 2009) revealed a list of roughly 120 SNPs that have been associated with T2D. The intersection of this set with the presently studied 272,423 SNPs produced 35 candidate risk SNPs.

rs2237892, rs7578597, rs8050136 rs1111875, rs12970134, rs1387153, rs1470579, rs1496653, rs1552224, rs163184, rs16861329, rs17168486, rs2007084, rs2261181, rs2334499, rs243021, rs2447090, rs2612035, rs340874, rs391300, rs3923113, rs4299828, rs4607517, rs4812829, rs5215, rs6795735, rs7041847, rs7178572, rs7612463, rs7756992, rs7903146, rs8042680, rs831571, rs896854, rs9470794

Only one of these, rs2237892, meets the conditions for being admissible, i.e., one of 15,000 odd potential loci almost 3 standard deviations from $Q_c$, and in the usual manner leads to a significant p-value.

On the basis that $Q_d/Q_c$=1.28 it has been said in the literature that if the rarer symbol is found then it is 28% more likely that it signifies T2D rather than normalcy. However the odds that this symbol will be found is only about 1 in 10 and so this is really a poor predictor of T2D, which is the reason that indicator analysis eliminates this as a candidate locus. By comparison, the top entry in Table 1 states that its symbol will be found roughly 1 in 6 times and if found signifies that it is 68% more likely to signify T2D. As such it is an order of magnitude more effective a predictor of T2D, which is the case for the listed entries of Table 1

Disease Prediction

The gold standard for determining the value of any classifier of disease is its ability to predict that disease. This section provides verification of the methodologies by providing virtually compelling evidence of disease prediction.

To test the predictive ability of indicators as disease classifiers a randomly chosen fixed percentage of the case and control sets are made to serve as the training set by which to determine a disease classifier, and then to interrogate the remaining test set for its success as a predictor. The results after doing this repeatedly are displayed in Table 2.

TABLE 2

| | Training fraction | | | | | |
|---|---|---|---|---|---|---|
| | .7 | .8 | .9 | .95 | .98 | .99 |
| Classifier size | 2,464 | 2,076 | 1,724 | 1,578 | 1,438 | 1,419 |
| Success Rate (%) | 62.4 | 57.0 | 53.1 | 52.7 | 54.4 | 55.0 |

In Table 2 the first line gives the training set fraction, the second the average size of the classifier and the third the predictive success rate.

For all cases of the table the criterion incremental information was taken as M=0.07, which was deemed to be better than other values. The number of trials was chosen so that there would be a strong likelihood that each sequence of the database would eventually appear in the test set at least once. For example for the training fraction of 0.99, there were 9 cases and 7 control sequences in east test set, randomly chosen in more than 1300 trials; for all other case there were at 500 trials. The indicator vector size and success rates represent averages over all trials.

The 70% partition clearly gives the best success rate and therefore was subjected to intense testing and the evidence for the 62.4% success rate of prediction is compelling; as is the evidence that with more data the success rate will become more robust Sirovich, 2014b Features and benefits or advantages of the invention over prior art approaches include:
1. A suite of novel methods for analyzing genomic (SNPs) data.
2. A suite of novel methods for analyzing type 2 diabetes T2D genomic data.
3. A novel method for predicting disease from genomic data.
4. A novel method for predicting T2D from genomic data.
5. A method which uniquely reorders genomic data for the first time in terms of allelic content.
6. The first application of the method to T2D.
7. A method which uniquely converts symbolic data to a correct digital representation.
8. A method for the vectorization of a genomic sequence.
9. The application of claims 7 & 9 to T2D data.
10. A method for selecting high value allele loci;
11. A new unbiased optimal selection of high value loci on the basis of information theoretic case/control incremental information (Shannon, 1948; Jaynes, 1955)
12. Applying Incremental Information analysis to T2D.
13. Determination of a disease classifier by application of the indicator method to potential high value loci of case/control databases.
14. Determination of T2D classifier.
15. Rank ordering classifiers on the basis of frequency of occurrence.
16. Creation of a single gene chip with the unique reporters for the classifier set of one particular disease, e.g. T2D.
17. Creation of a one or more gene chip(s) with reporters for the classifier set(s) of more than one disease.
18. A method for scoring disease by summing the classifier loci.
19. Association of a Chromosome with a disease, such as Chromosome 7 with T2D.

APPENDIX

The contents of each of the following references, copies of which are submitted herewith, are incorporated by reference as if fully set forth herein:

Jaynes, E. (1955). Information theory and statistical mechanics. Physical Review, 106, 620-630.

Sirovich, L. (2014a). Genomic Data and Disease Forecasting: Application to Type 2 Diabetes (T2D), PlosOne, 9, Issue 11e85684.

Sirovich, L. (2014b); Genomic Prediction of Disease: Application to T2D (type 2 diabetes), to be submitted for publication

---

The invention claimed is:

1. A method of identifying susceptibility of a patient to a predetermined complex hereditary disease derived from a large-scale genomic data first database composed of single nucleotide polymorphisms (SNPs) expressed as base pair symbols comprising the steps of:

accessing said first database of genomic data for said predetermined complex hereditary disease in the form of a matrix D, the rows of which are genomic sequences of disease subjects, and a comparison (control) matrix, C, of genomic sequences of control subjects deemed not to have the disease, the two matrices D &C having a common set of SNP columns and rows of numbers $N_d$ & $N_c$ respectively;

transforming the genomic data in said first database by organizing or registering it in terms of allele pairs to provide a modified second database and accompanied by listing of all SNP identities included in the first database through rs numbers that specify chromosomes, chromosome locations and the two nucleotide (base pair) symbols taken from [A,C,G,T] or it's integer alias [1, 2, 3, 4], unique pairs of SNP symbols (alleles) being arranged in anti-alphabetical (anti-integer) order, each SNP becoming a unique pair of alleles and pair of first and second nucleotide symbols replaced, without loss of information, by the integer 2 for the first symbol and the integer 1 for the second symbol so that, for example, if two relevant symbols are A and T, T=2 and A=1 the first allele becoming T=2 unless a SNP is homozygous, e.g., (A, A), in which case the allele pair is (1, 1);

digitizing said data in said modified second database by vectorization to enable analysis by a programmed computer by embedding symbol representations into vector form under the transformation 1→[1,0], 2→[0,1], whereby a SNP such as (A, T) transforms as (A,T)→ (T,A)→(2,1)→[0,1,1,0];

determining from said digitized data high value markers or loci of said predetermined complex hereditary disease through construction of Incremental Information, If, from D & C, by first determining probabilities based on symbol frequency at a particular locus, denoted by $p_d$ & $p_c$, respectively, and If is calculated from:

If=−([$p_d$ ln$_2$ $p_d$+(1−$p_d$)ln$_2$(1−$p_d$)]−[$p_c$ ln$_2$ $p_c$+(1−$p_c$)ln$_2$(1−$p_c$)]), which determines the excess of information in the diseased set over the controls that resides in an allele and leads to a reduced set of high value loci and symbols;

determining from said high value markers or loci an indicator vector determined by the criterion that this vector be optimally correlated with the disease population and minimally correlated with the control population, resulting in an eigenvector v defined by $$\frac{1}{N_d}D^\dagger Dv - \frac{1}{N_c}C^\dagger Cv = \lambda v,$$

where λ the largest eigenvalue;

determining from said indicator vector it's Alleles and Symbols to form a disease classifier as a two row matrix as follows:

$$\text{Classifier} = \begin{bmatrix} \text{Alleles} \\ \text{Symbols} \end{bmatrix},$$

for said predetermined complex hereditary disease calculating the amount of agreement of the disease sequences with the Classifier, termed the Score, and similarly calculating the Scores of normal (control) populations;

generating normal and disease probability distributions of database-derived disease and control scores over the derived range of genomic loci for the disease and normal (control) populations, the intersection of the two probability distributions defining a transition score that separates said database derived disease and control scores, said transition score serving as a disease/control threshold determinant for any putative sequence;

using a gene array that includes elements which report on the activity of the classifier loci;

obtaining a specimen from a patient containing the patient's genomic information;

analyzing the patient's genomic information with said gene array to obtain a patient-derived score from specific sites determined by said disease classifier; and predicting the patient's likelihood of having or not having the disease by comparing the patient-derived score with said transition score and predicting that the degree of probability of the patient not contracting the disease increases as the patient-derived score increasingly deviates from said transition score in the direction of increasing database-derived control scores and that the degree of probability of the patient contracting the disease increases as the patient-derived score increasingly deviates from said transition score in the direction of increasing database-derived disease scores.

2. A method as defined in claim 1, wherein said first database is accessed from a governmental or institutional repository of genomic databases.

3. A method as defined in claim 1, wherein said first genomic database is for Type 2 Diabetes (T2D).

4. A method as defined claim 1, wherein said first genomic database is obtained from the FUSION database as obtained from the NIH.

5. A method as defined in claim 1, wherein each SNP of the data is registered as an allele pair and designated as odd or even, and said transforming step comprises moving higher symbols to odd positions and aliasing it by "2".

6. A method as defined in claim 1, wherein the data is registered as an allele pair and designated as odd or even, and said transforming step comprises moving lower symbols to even positions and aliasing them by "1".

7. A method as defined in claim 1, wherein the data is registered as two allele pairs and designated as odd or even, and said transforming step comprises moving higher symbols to odd positions and aliasing them by "2" and the moving lower symbols to even positions and aliasing them by "1".

8. A method as defined in claim 1, wherein odd-ratio probability analysis is used as the mathematical sampling algorithm.

9. A method as defined in claim 1, wherein said digitizing step comprises the step of digitizing symbol data so that "1"→[1,0] and "2"→[0,1].

10. A method as defined in claim 1, wherein additional disease classifier results are saved or stored on a single gene chip.

11. A method as defined in claim 1, wherein said step of determining high value markers or loci employs incremental information to reduce sampling bias.

12. A method as defined in claim 1, further comprising the step of repairing and/or deleting faulty loci prior to transforming the data.

13. A method as defined in claim 1, wherein said scoring step comprises determination of a composite score reflecting the number of loci contributing to the susceptibility of a disease.

14. A method as defined in claim 1, wherein the method is applied to at least two complex disease including but not limited to alcoholism, Alzheimer's disease, asthma, autism, bipolar disorder, obesity, cancer, epilepsy, schizophrenia, Type 2 Diabetes and coronary disease, and classifiers for said at least two of said complex diseases are incorporated in said gene chip.

* * * * *